(12) United States Patent
Majlessi

(10) Patent No.: US 10,172,599 B2
(45) Date of Patent: Jan. 8, 2019

(54) VENO-MERSE/HARVESTER DEVICE

(71) Applicant: Heshmat Majlessi, Rye, NY (US)

(72) Inventor: Heshmat Majlessi, Rye, NY (US)

( * ) Notice: Subject to any disclaimer, the term of this patent is extended or adjusted under 35 U.S.C. 154(b) by 0 days.

(21) Appl. No.: 14/583,786

(22) Filed: Dec. 29, 2014

(65) Prior Publication Data

US 2015/0238176 A1 Aug. 27, 2015

Related U.S. Application Data

(62) Division of application No. 13/329,590, filed on Dec. 19, 2011, now abandoned.

(51) Int. Cl.

| A61B 1/00 | (2006.01) |
|---|---|
| A61B 17/00 | (2006.01) |
| A61B 1/05 | (2006.01) |
| A61B 17/3205 | (2006.01) |
| A61B 1/04 | (2006.01) |
| A61B 1/06 | (2006.01) |
| A61B 17/32 | (2006.01) |
| A61B 17/3203 | (2006.01) |
| A61F 2/06 | (2013.01) |
| A61M 19/00 | (2006.01) |
| A61B 90/00 | (2016.01) |

(52) U.S. Cl.
CPC .... *A61B 17/00008* (2013.01); *A61B 1/00016* (2013.01); *A61B 1/00045* (2013.01); *A61B 1/00087* (2013.01); *A61B 1/04* (2013.01); *A61B 1/05* (2013.01); *A61B 1/0676* (2013.01); *A61B 17/3203* (2013.01); *A61B 17/320016* (2013.01); *A61B 17/32053* (2013.01); *A61B 90/361* (2016.02); *A61F 2/062* (2013.01); *A61M 19/00* (2013.01); *A61B 2017/00296* (2013.01); *A61B 2217/007* (2013.01)

(58) Field of Classification Search
CPC ............... A61B 1/00137; A61B 17/00008
USPC ......... 600/127, 153, 156, 158, 183; 606/109
See application file for complete search history.

(56) References Cited

U.S. PATENT DOCUMENTS

| 2,788,787 A * | 4/1957 | Trace ............... A61B 17/00008 606/159 |
|---|---|---|
| 3,312,222 A * | 4/1967 | Dwyer ................... A61B 17/42 15/104.18 |
| 4,793,346 A * | 12/1988 | Mindich .......... A61B 17/00008 606/180 |
| 5,030,201 A * | 7/1991 | Palestrant ...... A61B 17/320725 600/568 |
| 5,061,245 A * | 10/1991 | Waldvogel ....... A61B 17/00008 604/170.01 |
| 5,197,971 A * | 3/1993 | Bonutti .............. A61B 17/0218 604/105 |

(Continued)

*Primary Examiner* — Timothy J Neal
*Assistant Examiner* — Jae Woo

(57) ABSTRACT

A veno-merse/harvester device having a handle portion, a hollow shaft portion, and a cutting portion. A fixed cannula system incorporated in the device improves the hydrostatic pressure, which allows efficient hydro-dissection with less retrograde leak of tumescent fluid and facilitates the separation of the vein from surrounding tissues with less bleeding. The veno-merse/harvester device may incorporate a camera system to allow direct visualization of the side branches to be ligated during a procedure. The self-adjustable cutting tip facilitates the forward advancement of the veno-merse/harvester device safely over a dilated portion of a vein.

3 Claims, 4 Drawing Sheets

(56) References Cited

U.S. PATENT DOCUMENTS

| | | | | |
|---|---|---|---|---|
| 5,217,007 A * | 6/1993 | Ciaglia | A61M 16/0472 | 128/200.26 |
| 5,290,278 A * | 3/1994 | Anderson | A61B 17/11 | 606/15 |
| 5,351,679 A * | 10/1994 | Mayzels | A61B 17/0218 | 600/214 |
| 5,353,784 A * | 10/1994 | Nady-Mohamed | A61B 17/0218 | 600/205 |
| 5,387,196 A * | 2/1995 | Green | A61B 17/34 | 128/908 |
| 5,395,311 A * | 3/1995 | Andrews | A61B 17/32072 | 604/22 |
| 5,509,900 A * | 4/1996 | Kirkman | A61M 25/0082 | 604/104 |
| 5,569,183 A * | 10/1996 | Kieturakis | A61B 17/00008 | 604/500 |
| 5,593,402 A * | 1/1997 | Patrick | A61B 17/29 | 604/902 |
| 5,634,935 A * | 6/1997 | Taheri | A61B 17/00008 | 604/96.01 |
| 6,129,661 A * | 10/2000 | Iafrati | A61B 1/042 | 600/114 |
| 6,193,653 B1 * | 2/2001 | Evans | A61B 17/00008 | 600/210 |
| 6,306,163 B1 * | 10/2001 | Fitz | A61B 17/22 | 606/198 |
| 6,312,443 B1 * | 11/2001 | Stone | A61B 17/025 | 606/198 |
| 6,338,735 B1 * | 1/2002 | Stevens | A61B 17/320758 | 128/898 |
| 6,540,722 B1 * | 4/2003 | Boyle | A61F 2/013 | 604/104 |
| 6,712,829 B2 * | 3/2004 | Schulze | A61B 17/11 | 606/149 |
| 6,830,575 B2 * | 12/2004 | Stenzel | A61F 2/95 | 606/108 |
| 6,971,988 B2 * | 12/2005 | Orban, III | A61B 10/04 | 600/104 |
| 7,163,547 B2 * | 1/2007 | Majlessi | A61B 17/00008 | 606/159 |
| 7,311,720 B2 * | 12/2007 | Mueller | A61B 17/0057 | 606/151 |
| 7,632,289 B2 * | 12/2009 | Majlessi | A61B 17/32053 | 606/159 |
| 7,951,077 B2 * | 5/2011 | Sayeg | A61B 17/02 | 600/201 |
| 7,988,619 B2 * | 8/2011 | Longo | A61B 1/0008 | 600/114 |
| 2001/0018596 A1 * | 8/2001 | Selmon | A61M 29/02 | 606/198 |
| 2003/0009130 A1 * | 1/2003 | Stecker | A61M 1/0084 | 604/104 |
| 2004/0133226 A1 * | 7/2004 | Buckman | A61B 17/3415 | 606/167 |
| 2005/0075659 A1 * | 4/2005 | Realyvasquez | A61B 17/0682 | 606/167 |
| 2005/0149106 A1 * | 7/2005 | DiPoto | A61B 17/0218 | 606/198 |
| 2005/0273133 A1 * | 12/2005 | Shluzas | A61B 17/3439 | 606/198 |
| 2006/0069404 A1 * | 3/2006 | Shluzas | A61B 17/02 | 606/198 |
| 2008/0058590 A1 * | 3/2008 | Saadat | A61B 1/00085 | 600/109 |
| 2008/0140189 A1 * | 6/2008 | Nguyen | A61F 2/2412 | 623/2.11 |
| 2008/0188880 A1 * | 8/2008 | Fischer | A61B 17/320016 | 606/170 |
| 2008/0249558 A1 * | 10/2008 | Cahill | A61B 17/3439 | 606/198 |
| 2011/0190806 A1 * | 8/2011 | Wittens | A61B 17/320725 | 606/200 |
| 2013/0158345 A1 * | 6/2013 | Majlessi | A61B 17/00008 | 600/104 |
| 2015/0100041 A1 * | 4/2015 | Harari | A61M 29/00 | 604/513 |
| 2015/0182334 A1 * | 7/2015 | Bourang | A61F 2/2433 | 623/2.11 |

\* cited by examiner

VENO-MERSE/HARVESTER DEVICE

FIELD OF THE INVENTION

The present invention relates to medical devices and in particular, a device for removal of veins from the body.

BACKGROUND OF THE INVENTION

Veins are typically removed from the lower and upper extremities of the body for treating varicose veins, as well as harvesting veins for bypass procedures. Many prior art devices have been used in the past 100 years for removing the varicose veins of the lower extremities. Virtually all of them require major anesthesia at the hospital with potential complications and post-operative pain.

The practice of varicose vein treatment has changed dramatically over the last 10 years, making it an out-patient and less painful procedure, without the need for major anesthesia. The inventor's original harvester device and its subsequent improved version, disclosed in U.S. Pat. Nos. 7,163,547 and 7,632,289 and incorporated herein by reference, are used to remove the varicose veins of the lower extremities under local (tumescent) anesthesia in an office setting.

In prior art harvester devices, the fluid used for tumescent anesthesia is injected via a moveable needle through the shaft of the device. Such moveable needle has limited forward pressure due to leakage of fluid in a retrograde manner. As a result, the effectiveness of hydro-dissection and the anesthetic agent are reduced.

Prior art harvester devices have a cutting tip that is fixed and of a predetermined size. During a vein harvesting procedure, segments of the long saphenous vein may become dilated as a result of the flow turbulence within these veins. An enlarged segment of the saphenous vein that is larger than the rest of the trunk may interfere with the forward advancement of the harvester device.

Prior art harvester devices also do not provide a direct visual field of the surrounding tissues and veins being harvested.

Therefore, there is a need for an improved harvester device that provides forward pressure to the tumescent anesthesia fluid for an effective hydro-dissection and anesthesia, a cutting tip that can accommodate enlarged segments of the vein being harvested and a visual field of the surrounding tissues and veins being harvester.

SUMMARY OF THE INVENTION

The veno-merse/harvester device of the present invention comprises a handle portion, a hollow shaft portion extending therefrom and a cutting portion at the distal end of the shaft portion.

The present invention provides a veno-merse/harvester device that allows effective hydro-dissection of veins from the body by providing a fixed cannula system. The fixed cannula system is incorporated into the harvester device of the present invention, with the injection port being part of the handle portion and the tip being part of the cutting portion. A one-way valve is provided in the cannula system to create much higher forward pressure of fluid used in the cannula system.

The present invention provides a veno-merse/harvester device that provides a camera system that allows direct visualization of the surrounding tissues and veins being harvested. The camera system is incorporated into the shaft portion and cutting end of the harvester device of the present invention.

The present invention provides a veno-merse/harvester device that allows effective forward advancement of the device over a dilated portion of a vein by providing a self-adjustable cutting tip. The cutting portion includes the self-adjustable cutting tip that has at least two sections that pivotally move to accommodate an enlarged vein.

The veno-merse/harvester device of the present invention may be used to easily remove the veins in the lower extremities (e.g., the long saphenous vein) as well as the straight veins in the upper extremities (e.g., the cephalic vein) using the power of hydro dissection to separate the veins from the surrounding tissues and fat, facilitating an effortless removal of the veins. Mixing of the dissection fluid with local anesthesia allows the anesthetization of tissue surrounding the vein, and when coupled with the one-way valve, allowing forward hydro-dissection, significantly easing the advancement of the device.

BRIEF DESCRIPTION OF THE DRAWINGS

Preferred embodiments of the present invention have been chosen for purposes of illustration and description and are shown in the accompanying drawings forming a part of the specification wherein.

DETAILED DESCRIPTION OF THE PREFERRED EMBODIMENTS

Figure 1:
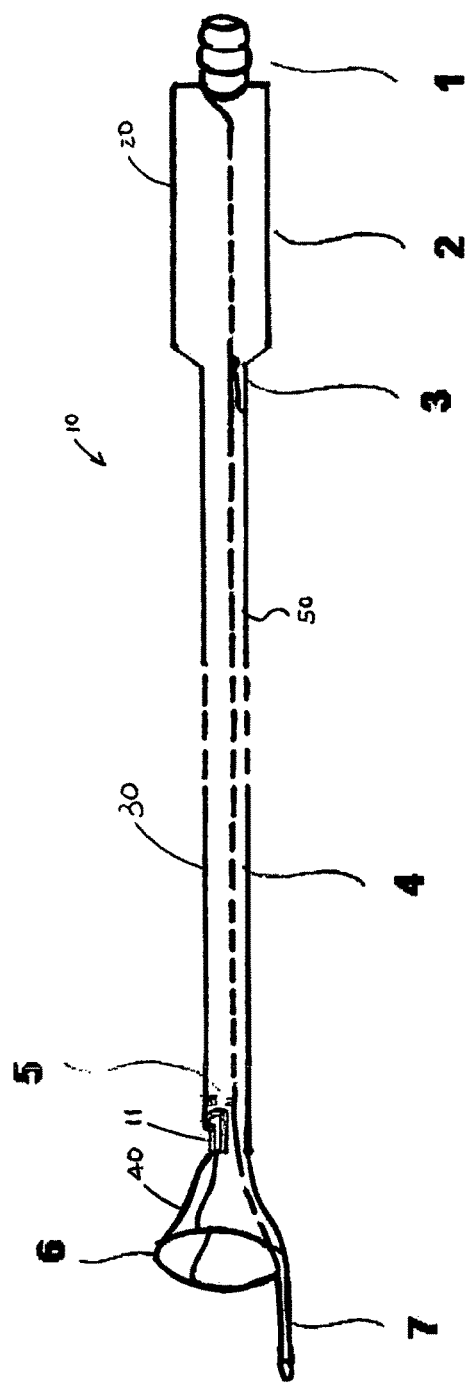
FIG. 1 is the harvester device of the present invention.
Figure 2:
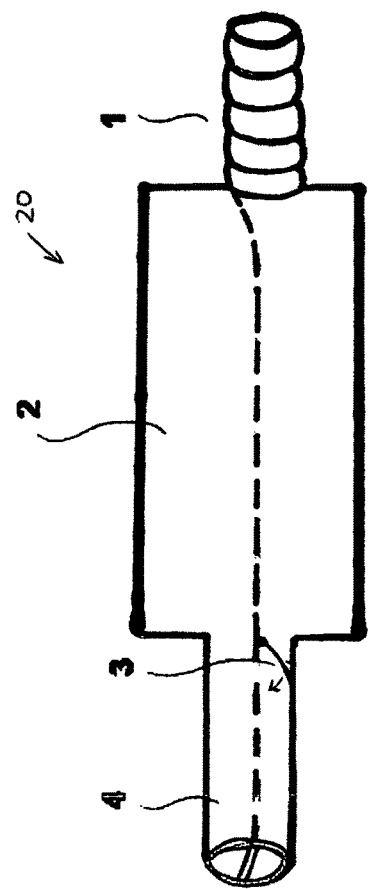
FIG. 2 is an enlarged view of the handle portion and shaft portion of the harvester device of the present invention showing an injection port and a one way valve within the shaft of the harvester device.
Figure 3:
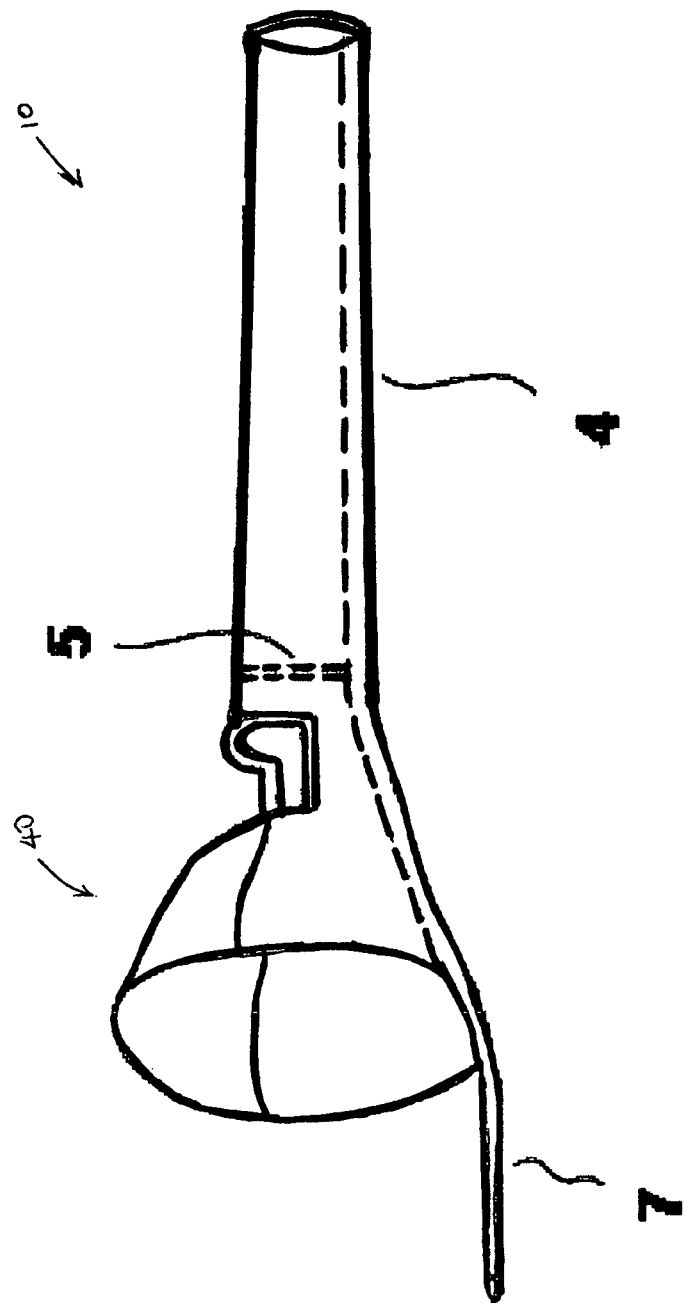
FIG. 3 is an enlarged view of the cutting end of the harvester device of the present invention showing a fixed cannula extending therefrom.

With reference to the drawings, wherein the same reference number indicates the same element throughout, there is shown in FIGS. 1-3 a veno-merse/harvester device 10 of the present invention comprises a handle portion 20, a hollow shaft portion 30, a cutting portion 40 and a cannula system 50.

The handle portion 20 is enlarged to allow the device 10 to be firmly gripped by a user. A user can control the forward advancement and rotation of the device 10 by directing or controlling the handle portion 20. Extending from the handle portion 20 is an elongated hollow shaft portion 30 having a generally smaller cross-section than the handle portion 20. At the distal end of the shaft portion 30 is the cutting portion 40. The shaft portion 30 is sealed at the junction 5 where it meets the cutting portion 40. The cutting portion 40 has an outwardly tapered, substantially frusto-conical shape with a circular cutting tip 6 at the distal end of the cutting portion 40 and an opening 11 near the proximal end of the cutting portion 40. The cutting tip 6 allows circular division of tissues and tributaries surrounding the vein without damaging the vein itself. The opening 11 allows percutaneous division of the vein using a small caliber blade inserted through the skin into or against the opening 11.

The cannula system 50 is incorporated into the handle portion 20, shaft portion 30 and the cutting portion 40 to form a closed system. An injection port 1 of the fixed cannula system 50 is provided in the handle portion 20 for receiving a fluid such as a tumescent fluid. The handle portion 20 and shaft portion 30 are hollow such that fluid can travel from the injection port 1 through the handle portion 20 and shaft portion 30 towards the cutting portion 40. Such fluid exits the cannula system 50 at tip 7, which is fixedly connected to and extends beyond the cutting tip 6 of the cutting portion 40. The cannula system 50 includes a one-way valve 3 such that fluid can only go in one direction, from the Injection port 1 to the tip 7.

The cannula system 50 of the present invention creates a closed system that advantageously provides a higher forward dissecting pressure than prior art devices for improved hydro-dissection. As a result, veins are easier to separate from surrounding tissues. Further, the added pressure against the veins advantageously compresses the veins, which are normally distended and full of blood, and reduces the bleeding from these compressed veins during the harvesting procedure and significantly reducing the bruising after surgery. Anesthesia injected through the cannula system 50 will be more effective than prior art devices as it travels further in the fatty tissue surrounding the veins with the one way valve 3 and extended tip 7, resulting in less pain during the vein harvesting procedure. The retrograde leakage of the anesthesia is also reduced as a result, which advantageously provides a drier operating field for the patient who is awake during the procedure. Further, the harvester device 10 is a more solid and stable instrument than prior art devices due to the fixed cannula system 50, without the need to move or re-insert the cannula repeatedly. Thereby, allowing the device 10 to be easily maneuvered and resulting in less pain to the patient during the procedure.

Figure 4:
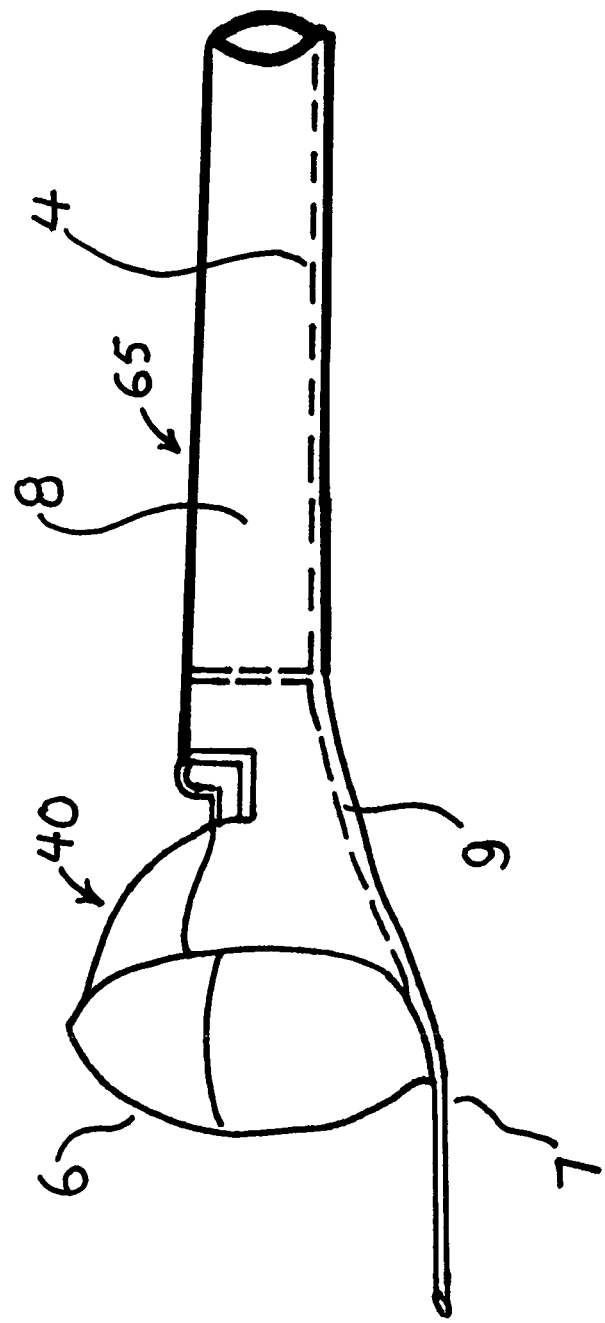
FIG. 4 is an enlarged view of the cutting end of an alternative embodiment of the harvester device of the present invention showing a wireless camera system within the cutting end.

In an alternate embodiment, as shown in FIG. 4, a veno-merse/harvester device 60 has a camera system 65. The camera system 65 includes a transmission device 8 and a camera 9. The camera 9 is located near the cutting tip 6 of the cutting portion 40 to allow direct visualizations of the side branches of the saphenous vein, allowing ligation from within or percutaneous ligation of these branches during coronary bypass harvesting. Lighting may be provided at the camera 9 to improve the visualization. Any transmission device 8 known to one skilled in the art may be used to transmit real-time visual imagery (stills or videos) received from the camera 9 wirelessly to a remote display device.

Figure 5:
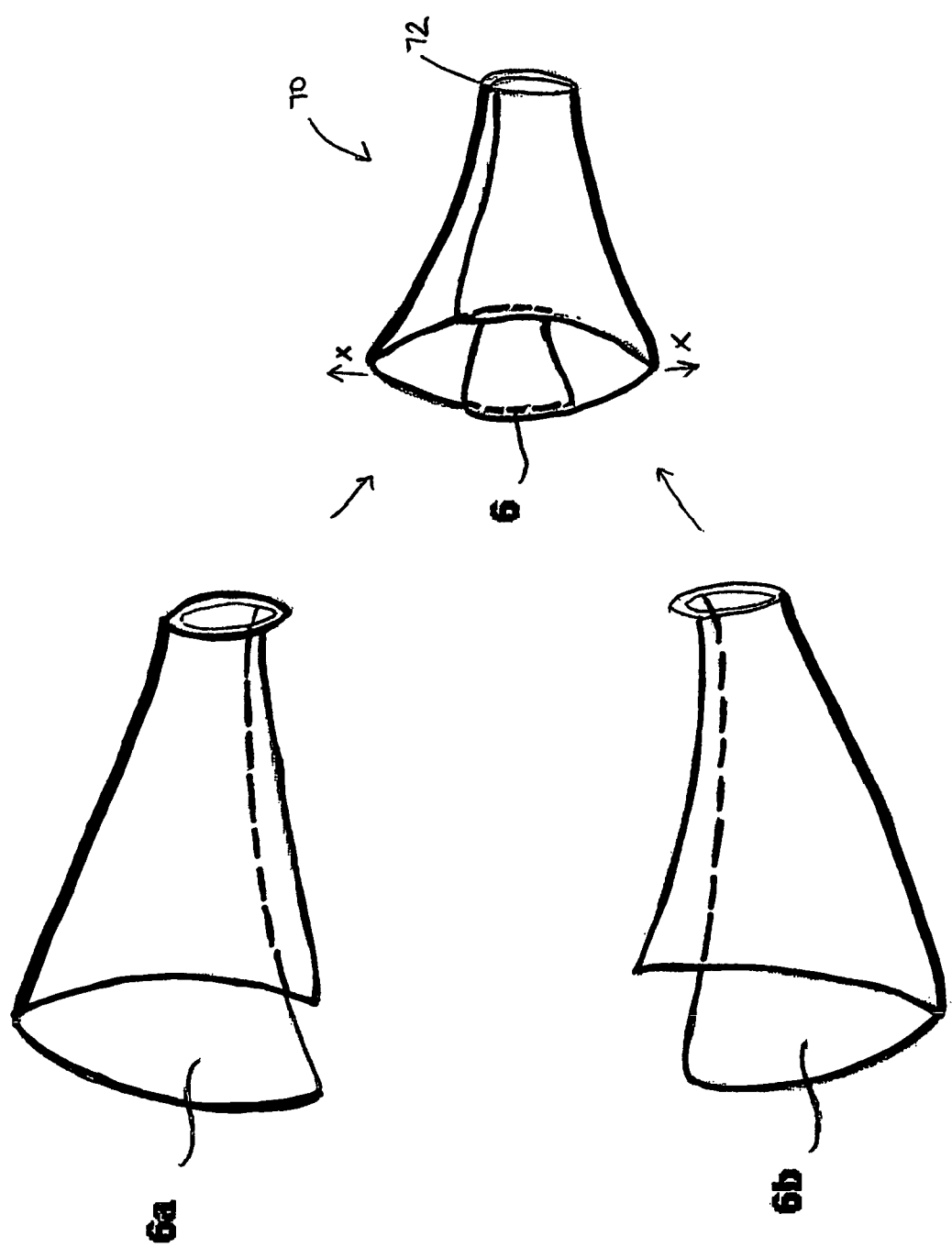
FIG. 5 is the self-adjustable cutting tip of the harvester device of the present invention.

An alternate cutting portion 70, as shown in FIG. 5, may be used with the veno-merse/harvester device 10 or 60 of the present invention or other prior art harvester devices. Cutting portion 70 includes two corresponding sections 6a and 6b. Sections 6a and 6b matingly form, with overlap, the outwardly tapered, substantially frusto-conical shape of the cutting portion 70. The distal end of sections 6a and 6b form the circular cutting tip 6. Sections 6a and 6b are hingedly or pivotally connected to each other at the end 72 where it meets the shaft portion 30 to allow the sections 6a and 6b to move in the direction of X. A spring or elastic (not shown) may be used to keep sections 6a and 6b at a predetermined distance apart or return sections 6a and 6b to a predetermined distance. When the harvester device 10 or 60 is advanced over a dilated portion of a vein, sections 6a and 6b will self-adjust and move in the direction of X, such that the diameter of the cutting tip 6 increases. While two sections 6a and 6b are shown in FIG. 5, 3 or more sections may be used to form the cutting portion 70.

The veno-merse/harvester device of the present invention as described above is less intrusive to a patient than the prior art devices. The present invention allows a faster and less painful procedure.

The features of the invention illustrated and described herein are the preferred embodiments. Therefore, it is understood that the appended claims are intended to cover the variations disclosed and unforeseeable embodiments with insubstantial differences that are within the spirit of the claims.

What I claim is:

1. A device for removing a saphenous vein from the body of patient comprising: a. a handle portion having first and second ends; b. a hollow shaft portion extending from said second end of said handle portion, said shaft portion having a distal end; c. a cutting portion extending from said distal end of said hollow shaft portion and forming a circular cutting tip defining an axis, said cutting portion being formed of a plurality of at least partially overlapping adjoining cutting sections circumferentially arranged about said axis, said cutting sections being hingedly or pivotably connected to each other at proximate ends thereof to allow said cutting sections to freely move radially inwardly towards said axis and radially outwardly away from said axis in response to external forces, decreasing the size of said circular cutting tip with maximum predetermined overlap of said adjoining cutting sections when radially inwardly-directed forces are applied to said cutting sections while allowing said cutting sections to be urged radially outwardly away from said axis to reduce overlap of adjoining cutting sections and increase the size of said circular tip in response to outwardly-directed forces applied to said cutting sections, whereby movement of said cutting portion along a saphenous vein within a saphenous tunnel causes the size of said circular cutting tip to self-adjust depending on the forces acting on said cutting sections as said cutting portion is moved along the vein between the vein and the saphenous tunnel through which the vein passes.

2. A device as defined in claim 1, wherein said cutting portion has a outwardly tapered shape.

3. A device as defined in claim 2 wherein said outwardly tapered shape is a substantially frusto-conical shape.

* * * * *